United States Patent
Tanioka

(10) Patent No.: US 10,052,588 B2
(45) Date of Patent: Aug. 21, 2018

(54) CONTROL APPARATUS, EXHAUST PURIFYING APPARATUS FOR INTERNAL COMBUSTION ENGINE, AND CONTROL METHOD FOR EXHAUST PURIFYING APPARATUS

(71) Applicant: Bosch Corporation, Tokyo (JP)

(72) Inventor: Kenichi Tanioka, Saitama (JP)

(73) Assignee: Bosch Corporation, Tokyo (JP)

(*) Notice: Subject to any disclaimer, the term of this patent is extended or adjusted under 35 U.S.C. 154(b) by 202 days.

(21) Appl. No.: 14/895,954

(22) PCT Filed: May 19, 2014

(86) PCT No.: PCT/JP2014/063193
§ 371 (c)(1),
(2) Date: Dec. 4, 2015

(87) PCT Pub. No.: WO2014/199777
PCT Pub. Date: Dec. 18, 2014

(65) Prior Publication Data
US 2016/0114289 A1    Apr. 28, 2016

(30) Foreign Application Priority Data
Jun. 10, 2013  (JP) .................................. 2013-121685

(51) Int. Cl.
*B01D 53/94* (2006.01)
*B01D 53/30* (2006.01)
(Continued)

(52) U.S. Cl.
CPC ......... *B01D 53/9495* (2013.01); *B01D 53/30* (2013.01); *B01D 53/9409* (2013.01);
(Continued)

(58) Field of Classification Search
CPC .... F01N 2560/026; F01N 3/208; F01N 11/00; F01N 11/002; F01N 2550/00;
(Continued)

(56) References Cited

U.S. PATENT DOCUMENTS

2010/0024394 A1* 2/2010 Kitazawa ........... B01D 53/9495
60/276
2010/0205940 A1   8/2010 Toshioka et al.
2012/0260634 A1  10/2012 Devarakonda et al.

FOREIGN PATENT DOCUMENTS

EP         2397663 A1   12/2011
JP      2005233117 A    9/2005
(Continued)

OTHER PUBLICATIONS

International Search Report for Application No. PCT/JP2014/063193 dated Jul. 8, 2014 (English Translation, 2 pages).

*Primary Examiner* — Dennis White
*Assistant Examiner* — Bryan Kilpatrick
(74) *Attorney, Agent, or Firm* — Michael Best & Friedrich LLP

(57) ABSTRACT

A control apparatus that includes a measured NOx purification ratio calculation unit calculating a measured NOx purification ratio of a reduction catalyst based on outputs of NOx sensors and provided upstream and downstream of the reduction catalyst reducing nitrogen oxide in an exhaust gas, an estimated NOx purification ratio calculation unit calculating an estimated NOx purification ratio of the reduction catalyst based on a temperature of the reduction catalyst, a flow rate of the exhaust gas, and an absorption amount of the reducing agent by the reduction catalyst, and a reducing agent concentration estimation unit estimating a concentration of the reducing agent injected from a reducing agent
(Continued)

64  UPSTREAM-OF-CATALYST NOx CONCENTRATION ACQUISITION UNIT
66  DOWNSTREAM-OF-CATALYST NOx CONCENTRATION ACQUISITION UNIT
62  UREA WATER INJECTION CONTROL UNIT
82  ABSORPTION AMOUNT ESTIMATION UNIT
80  INSTRUCTED INJECTION AMOUNT CORRECTION UNIT
72  MEASURED NOx PURIFICATION RATIO CALCULATION UNIT
70  ESTIMATED NOx PURIFICATION RATIO CALCULATION UNIT
74  NOx PURIFICATION RATIO INFLUENCE DEGREE CALCULATION UNIT
76  AQUEOUS UREA SOLUTION CONCENTRATION ESTIMATION UNIT
78  QUALITY SENSOR VALIDITY DETERMINATION UNIT
68  AQUEOUS UREA SOLUTION CONCENTRATION ACQUISITION UNIT injection valve based on the measured NOx purification ratio and the estimated NOx purification ratio.

11 Claims, 4 Drawing Sheets

(51) Int. Cl.
  *F01N 11/00* (2006.01)
  *F01N 3/20* (2006.01)
  *G01N 33/00* (2006.01)
(52) U.S. Cl.
  CPC ......... *B01D 53/9431* (2013.01); *F01N 3/208* (2013.01); *F01N 11/00* (2013.01); *B01D 2251/2062* (2013.01); *B01D 2251/2067* (2013.01); *F01N 2560/026* (2013.01); *F01N 2610/02* (2013.01); *F01N 2610/146* (2013.01); *F01N 2900/0601* (2013.01); *G01N 33/0037* (2013.01); *Y02T 10/24* (2013.01); *Y02T 10/47* (2013.01)

(58) Field of Classification Search
  CPC ......... F01N 2560/14; F01N 2900/0601; F01N 2900/1621; B01D 53/9431; B01D 53/30; B01D 53/9409; B01D 53/9495; F02D 41/146
  See application file for complete search history.

(56) References Cited

FOREIGN PATENT DOCUMENTS

| | | |
|---|---|---|
| JP | 2008240546 | 10/2008 |
| JP | 2010007568 | 1/2010 |
| JP | 2010106671 | 5/2010 |
| JP | 2012002060 | 1/2012 |
| JP | 2012107536 | 6/2012 |
| WO | 2010082354 | 7/2010 |
| WO | 2010095221 A1 | 8/2010 |

* cited by examiner

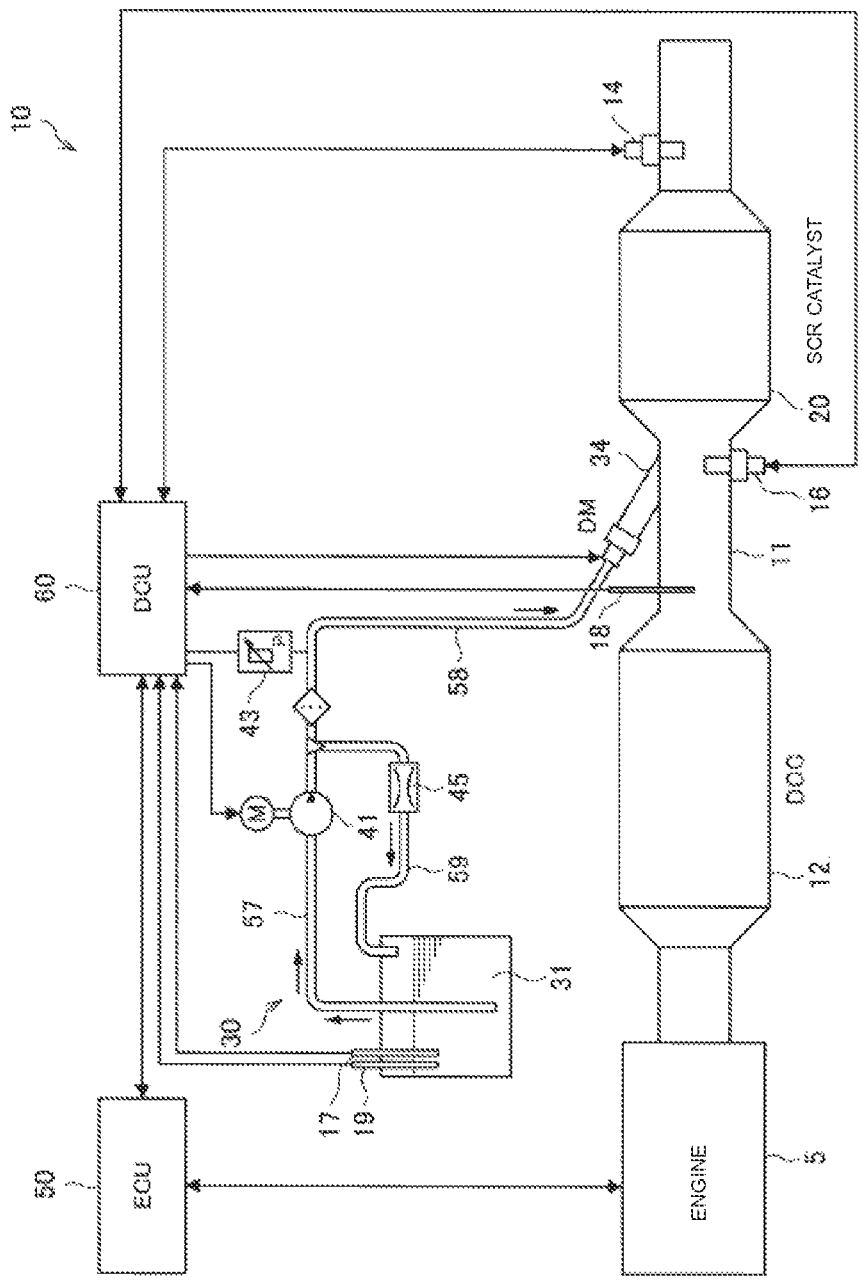
[Fig. 1]

[Fig.2]
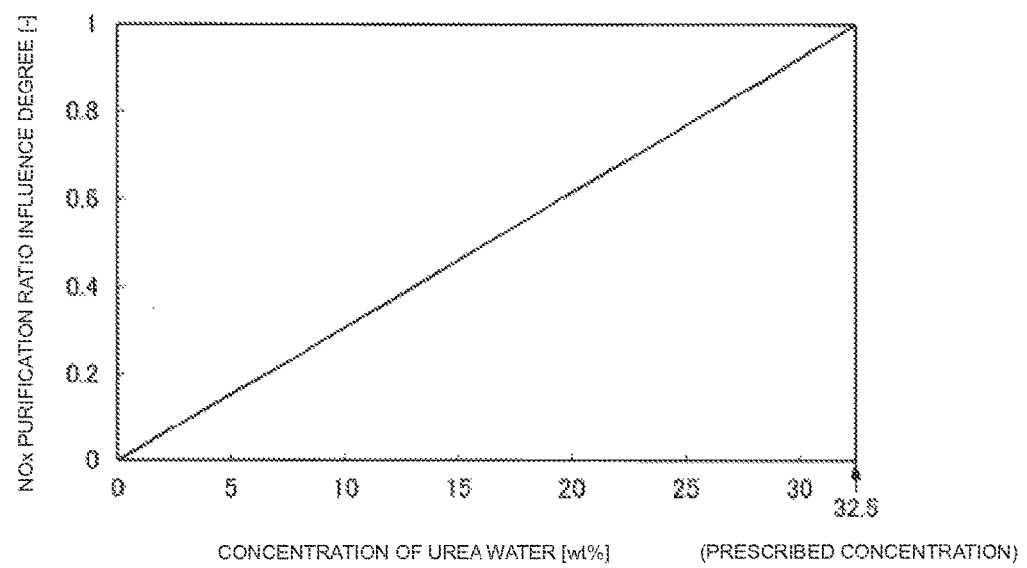

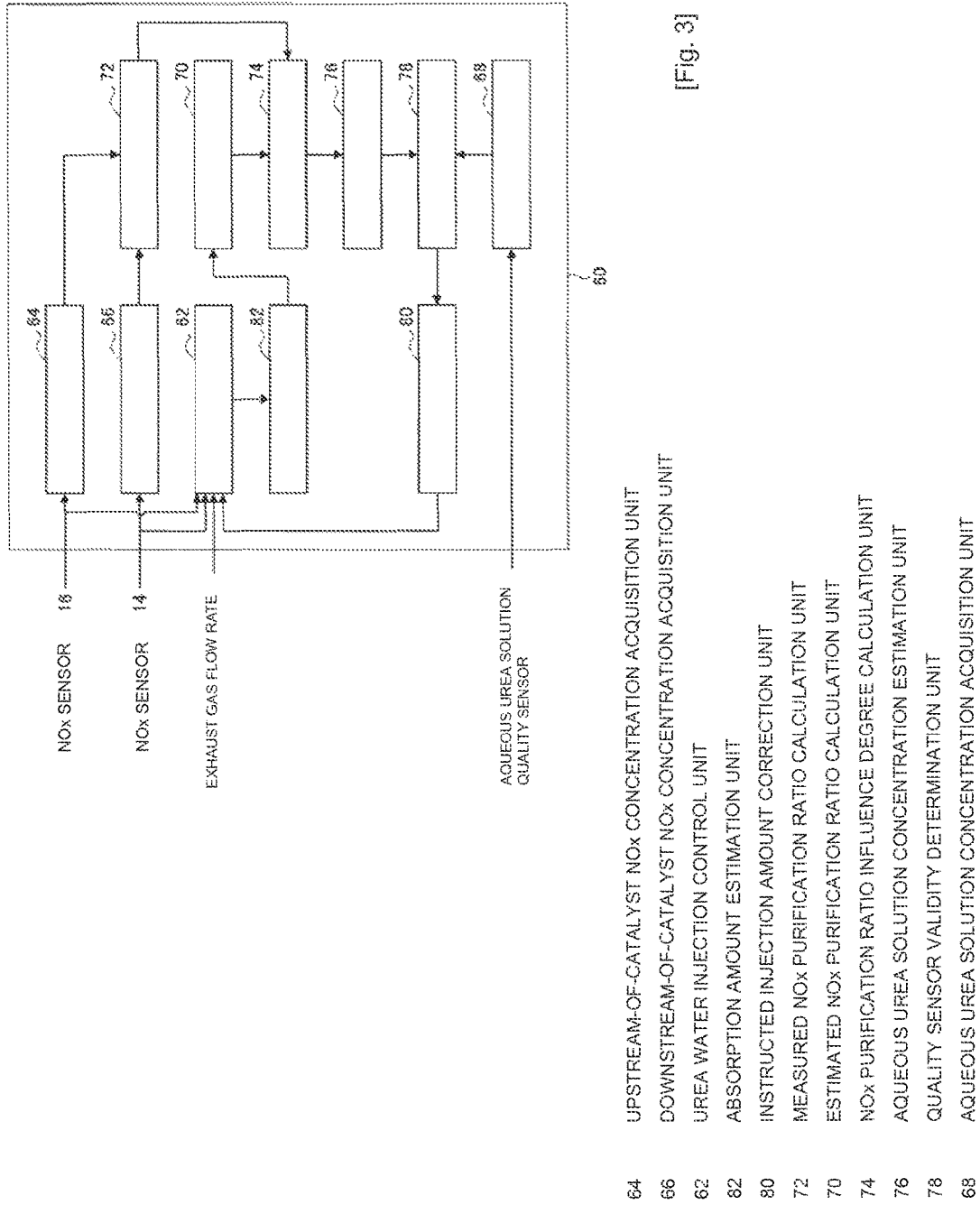

[Fig.4]

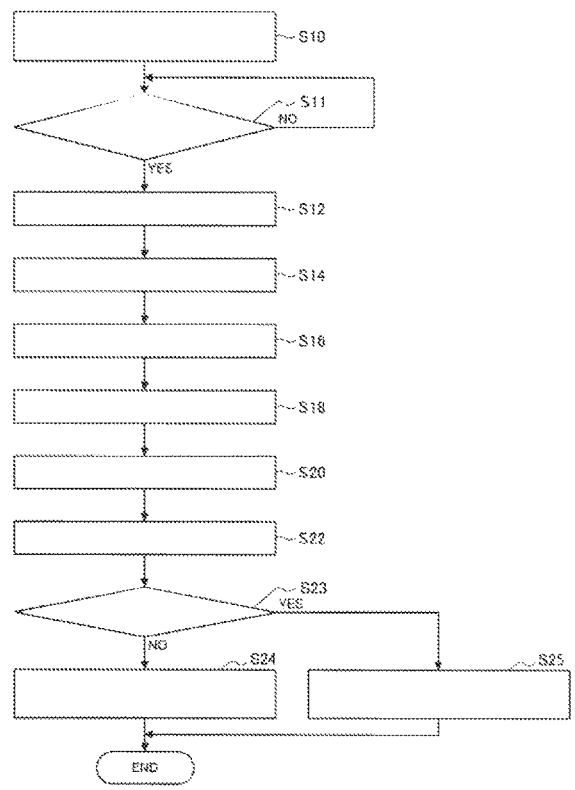

S10    OBTAIN CONCENTRATION OF AQUEOUS UREA SOLUTION FROM OUTPUT OF QUALITY SENSOR
S11    WHETHER CONCENTRATION OF AQUEOUS UREA SOLUTION IS LOWER THAN PRESCRIBED CONCENTRATION?
S12    OBTAIN UPSTREAM NOx CONCENTRATION AND DOWNSTREAM NOX CONCENTRATION
S14    CALCULATE ESTIMATED NOx PURIFICATION RATIO
S16    CALCULATE MEASURED NOx PURIFICATION RATIO
S18    CALCULATE NOx PURIFICATION RATIO INFLUENCE DEGREE
S20    ESTIMATE CONCENTRATION OF AQUEOUS UREA SOLUTION
S22    DETERMINE VALIDITY OF QUALITY SENSOR
S23    QUALITY SENSOR IS VALID?
S24    CORRECT INSTRUCTED INJECTION AMOUNT BASED ON ESTIMATED CONCENTRATION OF AQUEOUS UREA SOLUTION
S25    CORRECT INSTRUCTED INJECTION AMOUNT BASED ON SENSOR DETECTION CONCENTRATION

CONTROL APPARATUS, EXHAUST PURIFYING APPARATUS FOR INTERNAL COMBUSTION ENGINE, AND CONTROL METHOD FOR EXHAUST PURIFYING APPARATUS

BACKGROUND OF THE INVENTION

The present invention relates to a control apparatus, an exhaust purifying apparatus for an internal combustion engine, and a control method for an exhaust purifying apparatus.

Nitrogen oxide (NOx) may be included in an exhaust gas exhausted from an internal combustion engine installed in a vehicle or the like. Accordingly, there is a known system that has an injection valve upstream of a selective reduction type NOx catalyst apparatus (SCR) and reduces nitrogen oxide in the exhaust gas by injecting an ammoniacal solution supplied from an ammoniacal solution supply apparatus to an exhaust gas passage through the injection valve.

As for such a system using a reducing agent, JP-A-2008-240546 describes a technique for detecting the concentration of urea water stored in a storage tank using a concentration sensor. In addition, JP-A-2012-2060 describes a technique for determining the quality of the concentration if the detected temperature of urea water is higher than the lower limit of the determinable water temperature set individually in a system that detects the concentration and temperature of urea water in a urea tank.

SUMMARY OF THE INVENTION

In a system including a selective reduction type NOx catalyst apparatus (SCR), a reducing agent such as an aqueous urea solution injected to the catalyst may be diluted due to inclusion of water. In such a case, if error is introduced in an output of the concentration sensor for detecting the concentration of the reducing agent, the concentration of the reducing agent cannot be detected correctly.

If error is introduced in an output of the concentration sensor for detecting the concentration of the reducing agent, it is also difficult to appropriately control the injection amount of the reducing agent to be injected to the catalyst.

Accordingly, the invention addresses the above problems with the object of providing a novel and improved control apparatus, exhaust purifying apparatus for an internal combustion engine, and control method for exhaust purifying apparatus that are capable of accurately estimating the concentration of a reducing agent in a system including a reduction catalyst reducing nitrogen oxide by absorbing the reducing agent.

To solve the above problems, according to an aspect of the present invention, there is provided a control apparatus including a measured NOx purification ratio calculation unit calculating a measured NOx purification ratio of a reduction catalyst reducing nitrogen oxide in an exhaust gas based on outputs of NOx sensors provided upstream and downstream of the reduction catalyst, an estimated NOx purification ratio calculation unit calculating an estimated NOx purification ratio of the reduction catalyst based on a temperature of the reduction catalyst, a flow rate of the exhaust gas, and an absorption amount of the reducing agent by the reduction catalyst, and a reducing agent concentration estimation unit estimating a concentration of the reducing agent injected from the reducing agent injection valve based on the measured NOx purification ratio and the estimated NOx purification ratio.

The control apparatus may further include a quality sensor validity determination unit determining validity of an output of a quality sensor actually measuring a concentration of the reducing agent based on the concentration of the reducing agent estimated by the reducing agent concentration estimation unit.

The reducing agent concentration estimation unit may estimate the concentration of the reducing agent injected from the reducing agent injection valve based on the measured NOx purification ratio and the estimated NOx purification ratio when the concentration of the reducing agent actually measured by the quality sensor is equal to or less than a predetermined value.

The control apparatus may further include a NOx purification ratio influence degree calculation unit calculating a ratio of the measured NOx purification ratio to the estimated NOx purification ratio as a NOx purification ratio influence degree.

The control apparatus may further include an injection amount correction unit correcting an injection amount of the reducing agent from the reducing agent injection valve based on the estimated concentration of the reducing agent and a prescribed concentration of the reducing agent when the quality sensor validity determination unit determines that the output of the quality sensor is not valid.

The reducing agent concentration estimation unit may estimate the concentration of the reducing agent injected from the reducing agent injection valve based on the measured NOx purification ratio and the estimated NOx purification ratio when the absorption amount of the reducing agent by the reduction catalyst reaches a target absorption amount.

To solve the above problems, according to another aspect of the present invention, there is provided an exhaust purifying apparatus for an internal combustion engine including the above control apparatus.

To solve the above problems, according to another aspect of the present invention, there is provided a method for controlling an exhaust purifying apparatus including the steps of calculating a measured NOx purification ratio of a reduction catalyst reducing nitrogen oxide in an exhaust gas based on outputs of NOx sensors provided upstream and downstream of the reduction catalyst, calculating an estimated NOx purification ratio of the reduction catalyst based on a temperature of the reduction catalyst, a flow rate of the exhaust gas, and an absorption amount of the reducing agent by the reduction catalyst, and estimating a concentration of the reducing agent injected from the reducing agent injection valve based on the measured NOx purification ratio and the estimated NOx purification ratio.

The method may further include the step of determining validity of an output of a quality sensor actually measuring a concentration of the reducing agent based on the estimated concentration of the reducing agent.

The method may further include the step of determining whether the concentration of the reducing agent actually measured by the quality sensor is equal to or less than a predetermined value, in which the step of determining the concentration of the reducing agent may estimate a concentration of the reducing agent injected from the reducing agent injection valve based on the measured NOx purification ratio and the estimated NOx purification ratio when the concentration of the reducing agent actually measured by the quality sensor is equal to or less than a predetermined value.

The method may further include the step of calculating a ratio of the measured NOx purification ratio to the estimated NOx purification ratio as a NOx purification ratio influence degree.

The method may further include the step of correcting an injection amount of the reducing agent from the reducing agent injection valve based on the estimated concentration of the reducing agent and a prescribed concentration of the reducing agent when the output of the quality sensor is determined not to be valid.

The step of estimating the concentration of the reducing agent may estimate the concentration of the reducing agent injected from the reducing agent injection valve based on the measured NOx purification ratio and the estimated NOx purification ratio when the absorption amount of the reducing agent by the reduction catalyst reaches a target absorption amount.

According to the invention, the concentration of a reducing agent can be estimated accurately in a system including a reduction catalyst reducing nitrogen oxide by absorbing the reducing agent.

BRIEF DESCRIPTION OF THE DRAWINGS

FIG. 1 is a schematic view showing an example of the structure of an exhaust purifying apparatus for an internal combustion engine according to an embodiment of the present invention and peripheral components.

FIG. 2 is a characteristic diagram showing effects of a diluted aqueous urea solution on the NOx purification ratio influence degree when the concentration of the aqueous urea solution is lower than the prescribed concentration (=32.5 wt %).

FIG. 3 is a schematic view showing the functional blocks of components concerning the validity determination of a quality sensor in the structure of a control apparatus of the exhaust purifying apparatus according to the embodiment.

FIG. 4 is a flowchart showing the processing for determining the validity of the quality sensor.

DETAILED DESCRIPTION

Preferred embodiments of the present invention will be described in detail with reference to the drawings. In the specification and drawings, components having substantially the same functional structure are given the same reference numeral and descriptions are omitted.

FIG. 1 shows an example of the structure of an exhaust purifying apparatus 10 for an internal combustion engine according to an embodiment of the present invention and peripheral components. This exhaust purifying apparatus 10 is connected to an exhaust passage 11 of an internal combustion engine 5, includes a reduction catalyst 20, a reducing agent injection apparatus 30, a control apparatus 60, and so on, and is configured as a urea SCR system purifying nitrogen oxide (NOx) in an exhaust gas exhausted from the internal combustion engine 5 using an aqueous urea solution as a reducing agent. However, the reducing agent used in the present embodiment is not limited to an aqueous urea solution and may be, for example, ammonia water or the like, which can generate ammonia.

The internal combustion engine 5 is controlled by an ECU (engine control unit) 50. The control apparatus 60 receives control data and the like concerning control of the internal combustion engine 5 from the ECU 50. In the exhaust passage 11, an oxidation catalyst 12 (DOC) is disposed between the internal combustion engine 5 and the reduction catalyst 20. The oxidation catalyst 10 has a function of oxidizing carbon hydride (HC) and carbon monoxide (CO) in an exhaust gas. As the oxidation catalyst 12, a known catalyst is used as appropriate.

The reduction catalyst 20 used in the exhaust purifying apparatus 10 according to the embodiment has a function of absorbing ammonia generated by hydrolytic decomposition of an aqueous urea solution injected into the exhaust passage 11 and promoting a reduction reaction between ammonia and NOx. Specifically, in the reduction catalyst 20, ammonia ($NH_3$) generated by decomposition of urea in the aqueous urea solution reacts with NOx and NOx is decomposed into nitrogen ($N_2$) and water ($H_2O$). As the reduction catalyst 20, a known catalyst is used as appropriate.

A NOx sensor 14 for detecting the NOx concentration in an exhaust gas is provided downstream of the reduction catalyst 20. In addition, a NOx sensor 16 for detecting the NOx concentration in an exhaust gas is provided upstream of the reduction catalyst 20. Signals from the NOx sensors 14 and 16 are transmitted to the control apparatus 60 and the control apparatus 60 calculates the NOx concentration in the exhaust gas based on the sensor signals. In addition, an exhaust temperature sensor 18 is provided upstream of the reduction catalyst 20.

The reducing agent injection apparatus 30 includes a storage tank 31, a reducing agent injection valve 34, a pump 41, and so on as main components. The storage tank 31 and the pump 41 are interconnected by a first reducing agent supply passage 57 and the pump 41 and the reducing agent injection valve 34 are interconnected by a second reducing agent supply passage 58. Of these reducing agent supply passages, the second reducing agent supply passage 58 has a pressure sensor 43. The sensor signal of the pressure sensor 43 is transmitted to the control apparatus 60 and the control apparatus 60 calculates the pressure in the second reducing agent supply passage 58 based on this sensor signal.

In addition, a circulation passage 59 leading to the storage tank 31 is connected to an intermediate point in the second reducing agent supply passage 58. An orifice 45 is provided in the circulation passage 59 to give resistance to a flow of the reducing agent returned to the storage tank 31 via the circulation passage 59 and increase the pressure in the second reducing agent supply passage 58. In the storage tank 31, a tank temperature sensor 17 for detecting the temperature of the aqueous urea solution and a quality sensor 19 for detecting the quality of the aqueous urea solution are provided. The quality sensor 19 detects the quality of the aqueous urea solution in the storage tank 31, especially the concentration of the aqueous urea solution. Such a reducing agent injection apparatus may have a known structure.

As the pump 41, an electric pump driven and controlled by the control apparatus 60 is used. In the embodiment, the output of the pump 41 is fed back so that the pressure in the second reducing agent supply passage 58 detected by the pressure sensor 43 is maintained at a predetermined value.

As the reducing agent injection valve 34, an electromagnetically driven on-off valve opened or closed by the control apparatus 60 is used, and the reducing agent injection valve 34 is fixed to the part of the exhaust passage 11 upstream of the reduction catalyst 20. Basically, the energization control of the reducing agent injection valve 34 is performed in a state in which the pressure in the second reducing agent supply passage 58 is maintained at a target value. Specifically, the injection amount of the reducing agent into the exhaust passage 11 is adjusted by setting the valve-opening DUTY ratio during a predetermined DUTY cycle depending on an instructed injection amount obtained by calculation.

Here, the instructed injection amount Q of the reducing agent injection valve 34 can be calculated by expression (1) below.

Instructed injection amount Q=(Injection amount A equivalent to current NOx flow rate)+(Injection amount B equivalent to absorbable amount of reduction catalyst)     (1)

In expression (1), the injection amount A equivalent to the current NOx flow rate is the injection amount equivalent to the NOx flow rate in the exhaust gas flowing upstream of the reduction catalyst 20 and is the injection amount required to reduce NOx in the exhaust gas flowing upstream of the reduction catalyst 20. The NOx flow rate in the exhaust gas flowing upstream of the reduction catalyst 20 can be obtained by multiplying the flow rate of the exhaust gas by the NOx concentration calculated based on a sensor signal of the NOx sensor 16. The extra part of the injection amount exceeding the injection amount A equivalent to the NOx flow rate in the exhaust gas is equivalent to the amount (absorption amount of ammonia) absorbed by the reduction catalyst 20 at that time and control is made so that the extra part of the injection amount (injection amount B) equals the absorbable amount by the reduction catalyst. In addition, the injection amount B equivalent to the absorbable amount of the reduction catalyst 20 is calculated by subtracting the current absorption amount of ammonia by the reduction catalyst 20 from the total absorption amount that can be absorbed by the reduction catalyst 20 at the current catalyst temperature. The absorbable amount that can be absorbed by the reduction catalyst 20 is predetermined based on the characteristics of the reduction catalyst 20 and depends on the temperature of the catalyst. The total absorption amount that can be absorbed by the reduction catalyst 20 is set to a value approximately 80% of the maximum absorption amount that can be absorbed by the reduction catalyst 20 theoretically. Accordingly, the ammonia absorption amount by the reduction catalyst 20 is not saturated, thereby suppressing a leak of ammonia downstream.

The control apparatus 60 calculates the instructed injection amount Q using the above expression once a predetermined number of cycles and controls the injection amount from the reducing agent injection valve 34. The control apparatus 60 calculates the injection amount B equivalent to the absorbable amount by the catalyst once a predetermined number of cycles and integrates the calculated injection amount B with the injection amount B obtained in the previous cycle to obtain the ammonia absorption amount by the reduction catalyst 20 once a predetermined number of cycles.

The quality sensor 19 provided in the storage tank 31 detects the concentration of an aqueous urea solution. The aqueous urea solution is a solution having ideally the prescribed concentration (32.5 wt %) and, in this state, has the lowest freezing temperature (melting point) of the aqueous urea solution. On the other hand, if an abnormality occurs in an output value of the quality sensor 19, the concentration of the aqueous urea solution becomes inaccurate. When the concentration of the aqueous urea solution becomes inaccurate, the injection amount from the reducing agent injection valve 34 cannot be controlled optimally. If the concentration of the aqueous urea solution is lower than the prescribed concentration, the injection amount from the reducing agent injection valve 34 needs to be increased depending on the reduction in the concentration of the aqueous urea solution to obtain the NOx purification ratio assumed when the concentration of the aqueous urea solution equals the prescribed concentration. However, when the accurate concentration of the aqueous urea solution cannot be obtained based on an output value from the quality sensor 19, it is difficult to increase the injection amount depending on the reduction in the concentration of the aqueous urea solution. Accordingly, in the embodiment, the validity of an output of the quality sensor 19 is diagnosed based on the NOx purification ratio during injection of urea water from the reducing agent injection valve 34.

The determination of validity can be made when it is determined that the concentration of the aqueous urea solution differs from the prescribed concentration based on an output of the quality sensor 19. In this case, the NOx values upstream and downstream of the reduction catalyst 20 are integrated after the exhaust purifying apparatus 10 is started, the aqueous urea solution is injected from the reducing agent injection valve 34, and the amount of ammonia ($NH_3$) absorbed by the reduction catalyst 20 reaches a target absorption amount. In the integration, the detection values of the NOx sensors 14 and 16 upstream and downstream of the reduction catalyst 20 are integrated with each other and the NOx values upstream and downstream of the reduction catalyst 20 obtained by model calculation are integrated with each other. Then, the NOx purification ratios of the measured value and the model value are calculated based on the integration value of the NOx values upstream and downstream of the reduction catalyst 20 after an elapse of a certain time, the NOx purification ratio actually measured is compared with the NOx purification ratio obtained by the model calculation, and the validity of an output of the quality sensor 19 is determined based on the result of the comparison.

Here, the NOx purification ratio (estimated NOx purification ratio) of the model value can be obtained by expression (2) below.

Estimated NOx purification ratio=1−(Estimated downstream-of-catalyst NOx integrated value/Upstream-of-catalyst NOx integrated value)     (2)

In addition, the NOx purification ratio (measured NOx purification ratio) of the measured values of the NOx sensors 14 and 16 can be obtained by expression (3) below.

Measured NOx purification ratio=1−(Measured downstream-of-catalyst NOx integrated value/Upstream-of-catalyst NOx integrated value)     (3)

In expression (2) and expression (3), the upstream-of-catalyst NOx integrated value can be calculated by expression (4) below.

Upstream-of-catalyst NOx integrated value=∫ upstream-of-catalyst NOx mass flow rate·dt     (4)

In expression (4), the upstream-of-catalyst NOx mass flow rate [g/s] can be calculated by expression (5) below.

Upstream-of-catalyst NOx mass flow rate [g/s]=Upstream-of-catalyst NOx concentration [ppm]× $10^{-6}$×NOx molar mass [g/mol]/Exhaust gas molar mass [g/mol]×Exhaust gas mass flow rate [g/s]     (5)

In expression (5), the upstream-of-catalyst NOx concentration [ppm] is a model value or measured value. The NOx molar mass [g/mol] and exhaust gas molar mass [g/mol] can be predetermined values. The exhaust gas mass flow rate [g/s] is calculated according to the intake air amount and the fuel injection amount of the internal combustion engine 5 and can be obtained from the ECU 50. If a model value is assigned to the upstream-of-catalyst NOx concentration [ppm] in expression (5), the upstream-of-catalyst NOx mass flow rate [g/s] calculated from expression (5) is a model value and, if this value is assigned to expression (4), the estimated upstream-of-catalyst NOx integrated value is obtained. Similarly, a measured value obtained from the NOx sensor 16 upstream of the catalyst is assigned to the upstream-of-catalyst NOx concentration [ppm] in expression (5), the upstream-of-catalyst NOx mass flow rate [g/s] calculated from expression (5) is a measured value and, if this value is assigned to expression (4), the measured upstream-of-catalyst NOx integrated value is obtained. In expression (2) and expression (3), the upstream-of-catalyst NOx integrated value described as the denominators may be a measured value (measured upstream-of-catalyst NOx integrated value) or an estimated value (estimated upstream-of-catalyst NOx integrated value). However, the same value is used in both expression (2) and expression (3). That is, the difference between the estimated NOx purification ratio in expression (2) and the measured NOx purification ratio in expression (3) is that the downstream NOx integrated value, which is the numerator, in expression (2) is an estimated value and the downstream NOx integrated value in expression (3) is a measured value.

In addition, in expression (2), the estimated downstream-of-catalyst NOx integrated value can be calculated from expression (6) below.

$$\text{Estimated downstream-of-catalyst NOx integrated value} = \int \text{Estimated downstream-of-catalyst NOx mass flow rate} \cdot dt \quad (6)$$

In expression (6), the estimated downstream-of-catalyst NOx mass flow rate [g/s] can be calculated from expression (7) below.

$$\text{Estimated downstream-of-catalyst NOx mass flow rate [g/s]} = \text{Estimated downstream-of-catalyst NOx concentration [ppm]} \times 10^{-6} \times \text{NOx molar mass [g/mol]} / \text{Exhaust gas molar mass [g/mol]} \times \text{Exhaust gas mass flow rate [g/s]} \quad (7)$$

In addition, in expression (7), the estimated downstream-of-catalyst NOx concentration [ppm] can be calculated from expression (8) below.

$$\text{Estimated downstream-of-catalyst NOx concentration [ppm] Upstream-of-catalyst NOx concentration [ppm]} \times (1-\text{NOx purification ratio estimated value}) \quad (8)$$

In expression (8), the NOx purification ratio estimated value is estimated by the catalyst temperature (exhaust temperature) of the reduction catalyst 20, the ammonia absorption amount by the reduction catalyst 20, and the exhaust gas flow rate. The absorption amount of ammonia by the reduction catalyst 20 can be obtained by integrating the injection amount B equivalent to the absorbable amount expression (1) above.

In addition, in expression (3), the downstream-of-catalyst NOx integrated value can be calculated by expression (9) below.

$$\text{Downstream-of-catalyst NOx integrated value} = \int \text{Downstream-of-catalyst sensor NOx mass flow rate} \cdot dt \quad (9)$$

In expression (9), the downstream-of-catalyst sensor NOx mass flow rate [g/s] can be calculated by expression (10) below.

$$\text{Downstream-of-catalyst sensor NOx mass flow rate [g/s]} = \text{Downstream-of-catalyst sensor NOx concentration [ppm]} \times 10^{-6} \times \text{NOx molar mass [g/mol]} / \text{Exhaust gas molar mass [g/mol]} \times \text{Exhaust gas mass flow rate [g/s]} \quad (10)$$

In expression (10), the downstream-of-catalyst sensor NOx concentration is obtained based on an output of the NOx sensor 14 downstream of the reduction catalyst 20.

As described above, according to expression (2) to expression (10), the estimated NOx purification ratio and the measured NOx purification ratio can be calculated.

Then, based on the estimated NOx purification ratio calculated in expression (2) and the measured NOx purification ratio calculated in expression (3), the NOx purification ratio influence degree is calculated using expression (11) below.

$$\text{NOx purification ratio influence degree} = \text{Measured NOx purification ratio} / \text{Estimated NOx purification ratio} \quad (11)$$

Here, the difference between the estimated NOx purification ratio calculated in expression (2) and the measured NOx purification ratio calculated in expression (3) is the following one point.

When the downstream-of-catalyst NOx concentration is obtained, in the case of the estimated NOx purification ratio calculated in expression (2), the upstream-of-catalyst NOx concentration and the NOx purification ratio estimated value are used to calculate the downstream-of-catalyst NOx concentration. On the other hand, in the case of the measured NOx purification ratio calculated in expression (3), the measured downstream-of-catalyst NOx concentration is used.

The instructed injection amount Q in expression (1) is calculated by assuming the concentration of the aqueous urea solution to be the prescribed concentration (32.5 wt %). Similarly, the prescribed NOx purification ratio is calculated also based on the aqueous urea solution having the prescribed concentration.

Accordingly, when the actual concentration of urea water is equal to the prescribed concentration, the measured NOx purification ratio is theoretically the same as the estimated NOx purification ratio and the NOx purification ratio influence degree becomes 1. If the concentration of the aqueous urea solution is lower than the prescribed concentration, the measured NOx purification ratio becomes smaller than the estimated NOx purification ratio and the NOx purification ratio influence degree becomes smaller than 1.

FIG. 2 is a characteristic diagram showing effects of a diluted aqueous urea solution on the NOx purification ratio influence degree when the concentration of the aqueous urea solution is lower than the prescribed concentration (=32.5 wt %). As shown in FIG. 2, the concentration of urea water is proportional to the NOx purification ratio influence degree and, when the concentration of the aqueous urea solution is lower than the prescribed concentration, the value of the NOx purification ratio influence degree becomes smaller accordingly.

Therefore, by applying the NOx purification ratio influence degree obtained in expression (11) to the characteristics in FIG. 2, the actual concentration of the aqueous urea solution can be estimated. Then, by comparing the estimated concentration of the aqueous urea solution with the concentration of the aqueous urea solution obtained from an output of the quality sensor 19, the validity of the output value of the quality sensor 19 can be diagnosed.

The validity of the quality sensor 19 may be determined by giving a certain margin to the estimated concentration of the aqueous urea solution while considering the tolerance of the quality sensor 19 or the calculation accuracy or the like of the NOx purification ratio influence degree. In addition, the validity of the quality sensor 19 is preferably diagnosed based on an output value of the quality sensor 19 detected under temperature conditions in which the aqueous urea solution does not include water or urea crystals.

Then, the injection amount from the reducing agent injection valve 34 is corrected based on the estimated concentration of the aqueous urea solution. In this case, injection amount is corrected based on the urea water injection amount correction coefficient calculated in expression (12). The correction is performed by multiplying the instructed injection amount Q calculated in expression (2) by the urea water injection amount correction coefficient obtained in expression (12).

Urea water injection amount correction coefficient=Urea water prescribed concentration/ Estimated aqueous urea solution concentration (12)

When the output value of the quality sensor 19 is determined to be valid, the injection amount from the reducing agent injection valve 34 is corrected based on the sensor detection concentration obtained from the output value of the quality sensor 19. In this case, the injection amount is corrected based on the urea water injection amount correction coefficient calculated in expression (13). As in the above, the correction is performed by multiplying the instructed injection amount Q calculated in expression (2) by the urea water injection amount correction coefficient obtained in expression (13).

Urea water injection amount correction coefficient=Urea water prescribed concentration/ Sensor detection concentration (13)

As described above, the validity of the aqueous urea solution concentration obtained from the quality sensor 19 can be determined. When the output of the quality sensor 19 is not valid, the injection amount from the reducing agent injection valve 34 can be maintained at an appropriate value by correcting the instructed injection amount Q using the urea injection amount correction coefficient.

FIG. 3 shows the functional blocks of components concerning the validity determination of the quality sensor 19 in the structure of a control apparatus 60 of the exhaust purifying apparatus 10 according to the embodiment.

This control apparatus 60 includes a urea water injection control unit 62, an upstream-of-catalyst NOx concentration acquisition unit 64, a downstream-of-catalyst NOx concentration acquisition unit 66, an aqueous urea solution concentration acquisition unit 68, an estimated NOx purification ratio calculation unit 70, a measured NOx purification ratio calculation unit 72, a NOx purification ratio influence degree calculation unit 74, an aqueous urea solution concentration estimation unit 76, a quality sensor validity determination unit 78, an instructed injection amount correction unit 80, and an absorption amount estimation unit 82. This control apparatus 60 is configured centering on a microcomputer having a known structure and individual components are achieved by causing the microcomputer to execute programs.

The control apparatus 60 also includes a storage unit (not shown). This storage unit stores the calculation results in individual components, data maps prepared in advance, and so on. The storage unit includes a volatile memory (RAM: random access memory) or a non-volatile memory.

The urea water injection control unit 62 sets the valve-opening DUTY ratio in a predetermined DUTY cycle based on the instructed injection amount Q in expression (1) and, based on the valve-opening DUTY ratio, controls the valve operation of the reducing agent injection valve 34. The upstream-of-catalyst NOx concentration acquisition unit 64 obtains the NOx concentration upstream of the reduction catalyst 20 from the output of the NOx sensor 16. The downstream-of-catalyst NOx concentration acquisition unit 66 obtains the NOx concentration downstream of the reduction catalyst 20 from the output of the NOx sensor 14. The aqueous urea solution concentration acquisition unit 68 obtains the concentration of the aqueous urea solution in the storage tank 31 from the output of the quality sensor 19.

The estimated NOx purification ratio calculation unit 70 calculates the estimated NOx purification ratio based on expression (2) above. The measured NOx purification ratio unit 72 calculates the measured NOx purification ratio based on expression (3) above. The NOx purification ratio influence degree calculation unit 74 calculates the NOx purification ratio influence degree based on expression (11) above. The aqueous urea solution concentration estimation unit 76 estimates the concentration of the aqueous urea solution by applying the NOx purification ratio influence degree calculated by the NOx purification ratio influence degree calculation unit 74 to the characteristics in FIG. 2. The quality sensor validity determination unit 78 compares the concentration of the aqueous urea solution estimated by the aqueous urea solution concentration estimation unit 76 with the concentration of the aqueous urea solution obtained by the aqueous urea solution concentration acquisition unit 68 from the output of the quality sensor 19 and diagnoses the validity of the output of the quality sensor 19. When the output value of the quality sensor 19 is not valid, the instructed injection amount correction unit 80 obtains the urea water injection amount correction coefficient based on expression (12) and corrects the instructed injection amount Q using the urea water injection amount correction coefficient. In contrast, when the output value of the quality sensor 19 is valid, the instructed injection amount correction unit 80 obtains the urea water injection amount correction coefficient based on expression (13) and corrects the instructed injection amount Q using the urea water injection amount correction coefficient. The absorption amount estimation unit 82 estimates the absorption amount of ammonia by the reduction catalyst 20 by integrating the injection amount B equivalent to the absorbable amount in expression (1) above.

Next, based on the flowchart in FIG. 4, processing for determining the validity of the quality sensor will be described. The processing in FIG. 4 is basically performed by the control apparatus 60. First, in step S10, the concentration of the aqueous urea solution in the storage tank 31 is obtained from the output of the quality sensor 19. In the next step S11, a decision is made as to whether the concentration of the aqueous urea solution obtained in step S10 is lower than a prescribed concentration and, when the concentration is lower than the prescribed concentration, the processing proceeds to step S12. In contrast, when the concentration of the aqueous urea solution is equal to or higher than the prescribed concentration, the processing waits in step S11.

In step S12, the NOx concentrations upstream and downstream of the reduction catalyst 20 are obtained from outputs of the NOx sensors 14 and 16. In the next step S14, the estimated NOx purification ratio is calculated based on expression (2) above. In the next step S16, the measured NOx purification ratio is calculated based on expression (3) above.

In the next step S18, the NOx purification ratio influence degree is calculated based on expression (11) above. In the next step S20, the concentration of the aqueous urea solution is estimated by applying the NOx purification ratio influence degree calculated in step S18 to the characteristics in FIG. 2. In the next step S22, the concentration of the aqueous urea solution estimated in step S20 is compared with the concentration of the aqueous urea solution obtained in step S10 from the output of the quality sensor 19 and the validity of the output of the quality sensor 19 is determined. In step S23, the processing proceeds to the next step S24 when the output of the quality sensor is not valid or the processing proceeds to the next step S25 when the output of the quality sensor is valid. In step S24, the urea water injection amount correction coefficient is obtained based on expression (12) and the instructed injection amount is corrected using the urea water injection amount correction coefficient. In step S25, the urea water injection amount correction coefficient is obtained based on expression (13) and the instructed injection amount is corrected using the urea water injection amount correction coefficient. Upon completion of step S24 or step S25, the processing ends (END).

As described above, according to the embodiment, the validity of the concentration of the aqueous urea solution obtained from the output of the quality sensor 19 can be diagnosed by calculating the NOx purification ratio influence degree based on the estimated NOx purification ratio and the measured NOx purification ratio. When the output of the quality sensor 19 is not valid, reduction in the NOx purification ratio can be suppressed by correcting the instructed injection amount based on the concentration of the estimated concentration of the aqueous urea solution. Accordingly, even when the concentration of the aqueous urea solution differs from the prescribed concentration, the NOx in an exhaust gas can be purified optimally.

Although a preferred embodiment has been described in detail above with reference to the drawings, the invention is not limited to the above examples. It is clear that persons having general knowledge in the technical field to which the invention belongs easily find various changes or modifications within the scope of the technical concepts described in the appended claims and the changes or modifications are also included in the technical scope of the invention.

The invention claimed is:

1. A control apparatus comprising:
    a measured NOx purification ratio calculation unit configured to calculate a measured NOx purification ratio of a reduction catalyst reducing nitrogen oxide in an exhaust gas based on outputs of NOx sensors provided upstream and downstream of the reduction catalyst;
    an estimated NOx purification ratio calculation unit configured to calculate an estimated NOx purification ratio of the reduction catalyst based on a temperature of the reduction catalyst, a flow rate of the exhaust gas, and an absorption amount of the reducing agent by the reduction catalyst;
    a reducing agent concentration estimation unit configured to estimate a concentration of the reducing agent injected from the reducing agent injection valve based on the measured NOx purification ratio and the estimated NOx purification ratio; and
    a quality sensor validity determination unit configured to determine a validity of an output of a quality sensor actually measuring a concentration of the reducing agent based on the concentration of the reducing agent estimated by the reducing agent concentration estimation unit.

2. The control apparatus according to claim 1, wherein the reducing agent concentration estimation unit is configured to estimate the concentration of the reducing agent injected from the reducing agent injection valve based on the measured NOx purification ratio and the estimated NOx purification ratio when the concentration of the reducing agent actually measured by the quality sensor is equal to or less than a predetermined value.

3. The control apparatus according to claim 1, further comprising:
    a NOx purification ratio influence degree calculation unit configured to calculate a ratio of the measured NOx purification ratio to the estimated NOx purification ratio as a NOx purification ratio influence degree.

4. The control apparatus according to claim 1, further comprising:
    an injection amount correction unit configured to correct an injection amount of the reducing agent from the reducing agent injection valve based on the estimated concentration of the reducing agent and a prescribed concentration of the reducing agent when the quality sensor validity determination unit determines that the output of the quality sensor is not valid.

5. The control apparatus according to claim 1, wherein the reducing agent concentration estimation unit is configured to estimate the concentration of the reducing agent injected from the reducing agent injection valve based on the measured NOx purification ratio and the estimated NOx purification ratio when the absorption amount of the reducing agent by the reduction catalyst reaches a target absorption amount.

6. An exhaust purifying apparatus for an internal combustion engine, comprising:
    a control apparatus including a measured NOx purification ratio calculation unit configured to calculate a measured NOx purification ratio of a reduction catalyst reducing nitrogen oxide in an exhaust gas based on outputs of NOx sensors provided upstream and downstream of the reduction catalyst;
    an estimated NOx purification ratio calculation unit configured to calculate an estimated NOx purification ratio of the reduction catalyst based on a temperature of the reduction catalyst, a flow rate of the exhaust gas, and an absorption amount of the reducing agent by the reduction catalyst;
    a reducing agent concentration estimation unit configured to estimate a concentration of the reducing agent injected from the reducing agent injection valve based on the measured NOx purification ratio and the estimated NOx purification ratio; and
    a quality sensor validity determination unit configured to determine a validity of an output of a quality sensor actually measuring a concentration of the reducing agent based on the concentration of the reducing agent estimated by the reducing agent concentration estimation unit.

7. A method for controlling an exhaust purifying apparatus comprising the steps of:
    calculating a measured NOx purification ratio of a reduction catalyst reducing nitrogen oxide in an exhaust gas based on outputs of NOx sensors provided upstream and downstream of the reduction catalyst;
    calculating an estimated NOx purification ratio of the reduction catalyst based on a temperature of the reduction catalyst, a flow rate of the exhaust gas, and an absorption amount of the reducing agent by the reduction catalyst;

estimating a concentration of the reducing agent injected from the reducing agent injection valve based on the measured NOx purification ratio and the estimated NOx purification ratio; and determining validity of an output of a quality sensor actually measuring a concentration of the reducing agent based on the estimated concentration of the reducing agent.

8. The method for controlling an exhaust purifying apparatus according to claim 7, further comprising the step of:

determining whether the concentration of the reducing agent actually measured by the quality sensor is equal to or less than a predetermined value, wherein the step of estimating the concentration of the reducing agent estimates a concentration of the reducing agent injected from the reducing agent injection valve based on the measured NOx purification ratio and the estimated NOx purification ratio when the concentration of the reducing agent actually measured by the quality sensor is equal to or less than a predetermined value.

9. The method for controlling an exhaust purifying apparatus according to claim 7, further comprising the step of:

calculating a ratio of the measured NOx purification ratio to the estimated NOx purification ratio as a NOx purification ratio influence degree.

10. The method for controlling an exhaust purifying apparatus according to claim 7, further comprising the step of:

correcting an injection amount of the reducing agent from the reducing agent injection valve based on the estimated concentration of the reducing agent and a prescribed concentration of the reducing agent when the output of the quality sensor is determined not to be valid.

11. The method for controlling an exhaust purifying apparatus according to claim 7, wherein the step of estimating the concentration of the reducing agent estimates the concentration of the reducing agent injected from the reducing agent injection valve based on the measured NOx purification ratio and the estimated NOx purification ratio when the absorption amount of the reducing agent by the reduction catalyst reaches a target absorption amount.

* * * * *